(12) United States Patent
Weiss

(10) Patent No.: US 7,472,706 B2
(45) Date of Patent: Jan. 6, 2009

(54) TRACHEOSTOMY TUBE PILLOW

(76) Inventor: Sondra L. Weiss, 2158 Cartwright Pl., Reston, VA (US) 20181

(*) Notice: Subject to any disclaimer, the term of this patent is extended or adjusted under 35 U.S.C. 154(b) by 478 days.

(21) Appl. No.: 11/236,298

(22) Filed: Sep. 27, 2005

(65) Prior Publication Data
US 2006/0065272 A1  Mar. 30, 2006

Related U.S. Application Data

(60) Provisional application No. 60/612,799, filed on Sep. 27, 2004.

(51) Int. Cl.
*A61M 11/00* (2006.01)
(52) U.S. Cl. ............................. 128/207.17; 128/207.14
(58) Field of Classification Search ............ 128/207.17, 128/207.14
See application file for complete search history.

(56) References Cited

U.S. PATENT DOCUMENTS

| | | | | | |
|---|---|---|---|---|---|
| 3,581,570 | A | * | 6/1971 | Wortz | 600/549 |
| 5,509,409 | A | * | 4/1996 | Weatherholt | 128/207.18 |
| 5,636,630 | A | * | 6/1997 | Miller et al. | 128/207.17 |
| 6,026,811 | A | * | 2/2000 | Settle | 128/207.17 |
| 6,336,457 | B1 | * | 1/2002 | Hudson et al. | 128/207.17 |
| 2006/0289011 | A1 | * | 12/2006 | Helsel | 128/207.17 |

* cited by examiner

*Primary Examiner*—Steven O Douglas
(74) *Attorney, Agent, or Firm*—Shoemaker and Mattabe

(57) ABSTRACT

A tubular foam pillow or cushion is placed against the neck of a patient below a tracheostomy tube, to improve comfort. The pillow is secured in place by means of a tie which passes lengthwise through the pillow. The tie may be of shoelace-like material, tied behind the neck, or it may have a Velcro-type surface which can attach to the surface of a tracheostomy collar.

8 Claims, 3 Drawing Sheets

TRACHEOSTOMY TUBE PILLOW

This application claims priority benefit from provisional patent application No. 60/612799, filed Sep. 27, 2004.

BACKGROUND OF THE INVENTION

This invention relates to a tracheostomy tube pillow.

In a standard tracheostomy, an incision is made through the throat of a patient into the trachea, and a tube is then inserted into the trachea through the incision.

SUMMARY OF THE INVENTION

An object of the invention is to improve comfort for a tracheostomy patient. A related object is to improve patient comfort in the area of the neck adjacent the tracheostomy tube.

The tracheostomy tube support can be used by both the ventilated and non ventilated tracheostomy patient to increase their comfort levels.

The support is preferably made of a closed-cell crosslinked polyolefin, a non latex, low absorption, light weight, flexible "soft skin" foam product which is secured to the tracheostomy collar with a hook and loop tie or around the neck with the cotton tie.

On the freshly trached patient, especially a patients whose trach tube has been stitched in, supporting the weight of the ventilator tubing decreases the pull on the tissue, thus improving comfort.

For patients who deflate their cuffs, the invention helps support the tracheostomy tube so it does not pull forward or move, which could cause internal damage and irritation, and making the trach tube is less likely to come out.

BRIEF DESCRIPTION OF THE DRAWINGS

In the accompanying drawing.

DESCRIPTION OF THE PREFERRED EMBODIMENT

Figure 1:
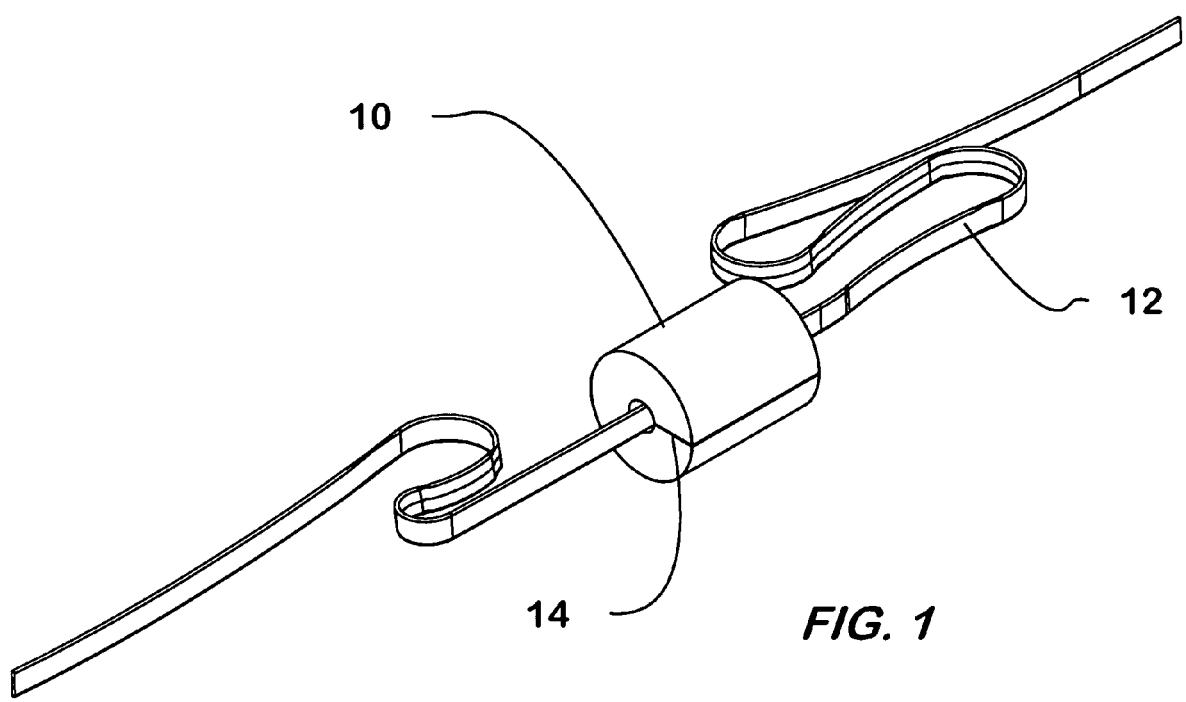
FIG. 1 is a perspective view of a tracheostomy tube pillow embodying the invention.

A tracheostomy tube pillow or cushion embodying the invention (FIG. 1) includes a soft sleeve 10, preferably made of a foam material, with a cotton tie 12 passing through the sleeve.

The tie is preferably a cotton string similar in construction to a shoestring. A presently preferred length of 30-36 inches provides ends of substantial length for easy tying.

I presently prefer that the sleeve be made of a soft, skinned, closed-cell polymeric foam such as "Microcell" (a registered trademark of Sentinel Products Corp., Hyannis, Mass.), and have a length of about 2.5 inches, an outer diameter of about two inches, and an inner diameter of about half an inch. The "skin" forms at least the outer surface of the sleeve. The best dimensions will depend in part on the situation, and may be optimized to values other than those stated above. Considering the range of potential patient sizes, it is anticipated that ties and sleeves of different sizes may conveniently be produced and sold as a kit.

The sleeve may be closed, in which case the tie is inserted lengthwise through the center of the sleeve, or it may have a lengthwise slit 14 as illustrated, in which case the tie can be passed laterally through the slit to the sleeve center. The inner diameter of the sleeve preferably exceeds the greatest width of the tie, so that the sleeve can slide freely on the tie; however, to prevent free sliding, the inner diameter could be reduced.

In use, the tie is placed around the neck and its ends, drawn lightly together, are tied behind the neck. The sleeve may then be repositioned between the tracheostomy tube and the neck of the patient, so that it supports the tube just below the incision.

Figure 2:
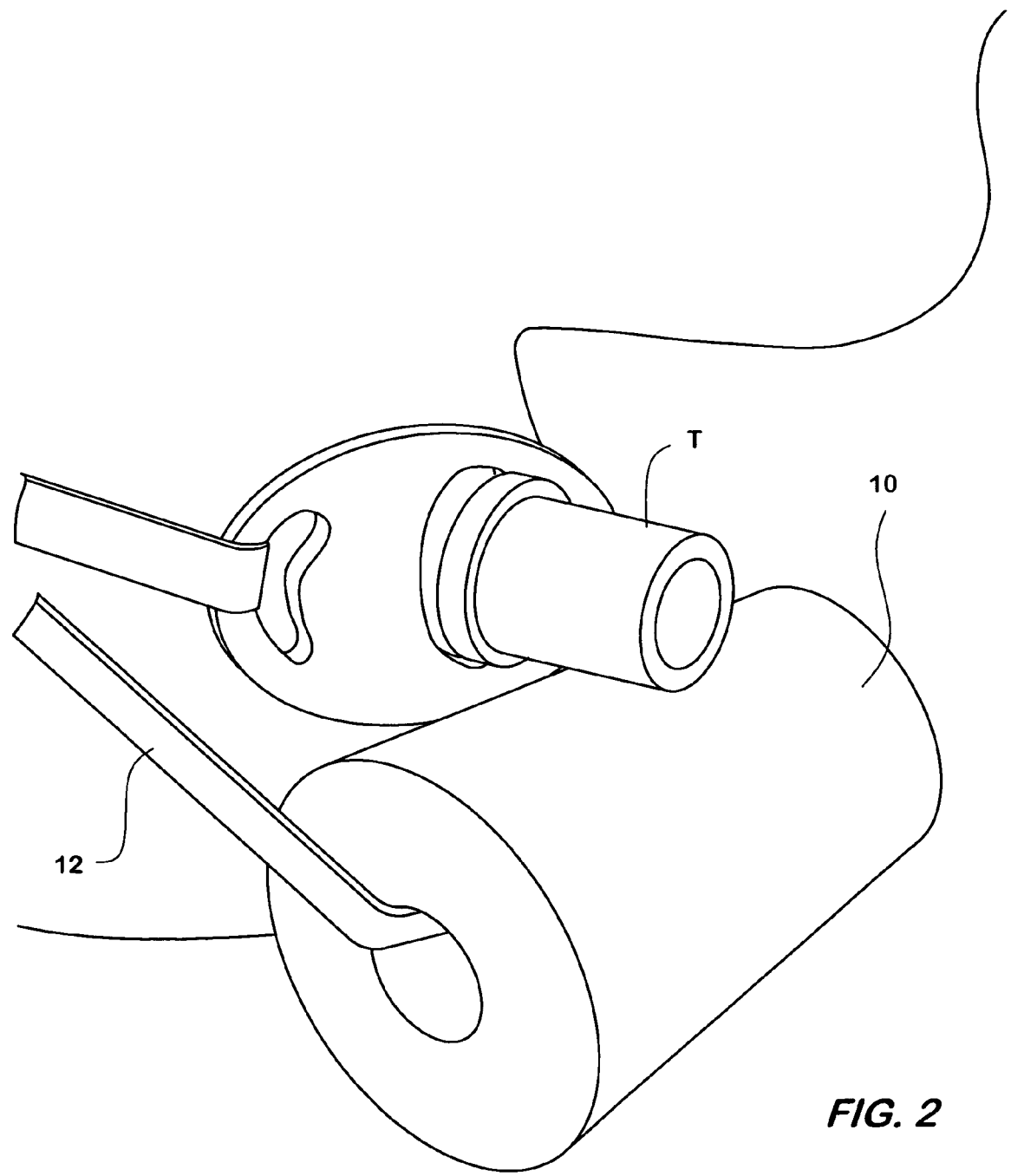
FIG. 2 shows the tube pillow installed on a patient's neck.
Figure 3:
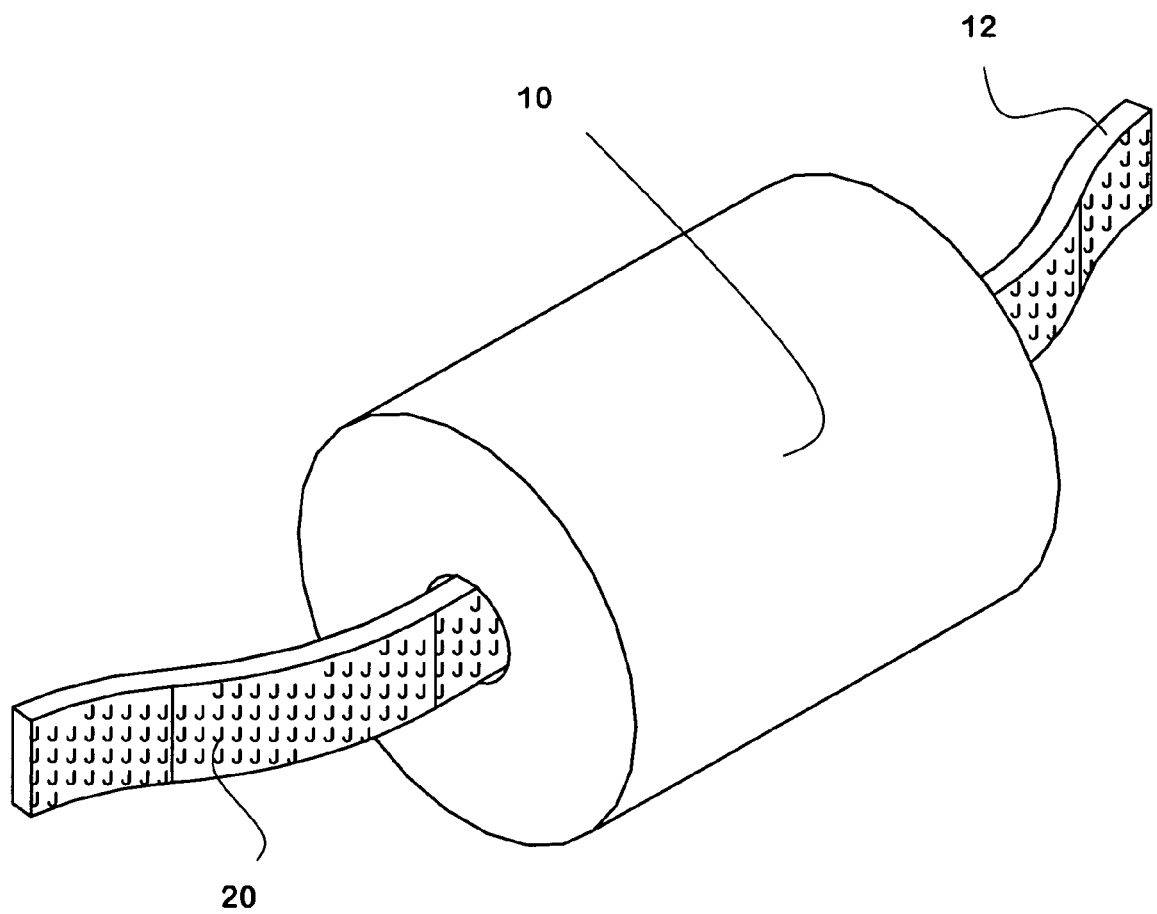
FIG. 3 is a perspective view of an alternative embodiment of the invention.

FIG. 2 shows an alternative embodiment in which the tie is replaced by a strip of material having hook elements 20 (e.g., "Velcro", a registered trademark of Velcro Industries B.V., Netherlands) on at least one surface. This embodiment makes it unnecessary to pass the ties around the back of the neck, or to form a knot in the ties, simplifying installation.

The "Velcro" strap is inserted through the sleeve hole, so that it extends about one and a half to two inches on either side of the sleeve. The protruding ends of the strap now can be stuck to a suitable fabric collar, worn on the neck. One such tracheostomy collar, having a fabric outer surface, is available from Dale Medical Products, Plainville, Mass. Alternatively, the collar could also have a "Velcro" surface (the complementary loop portion) on its outer surface. Either type of surface is called a "complementary" surface in the claims below. The best dimensions for the strap and the collar may be determined by routine experimentation.

Since the invention is subject to modifications and variations, it is intended that the foregoing description and the accompanying drawings shall be interpreted as only illustrative of the invention. Numerous modifications are possible. For example, the tie could be made of a non-cotton fabric, a non-woven fabric, or numerous other materials meeting the requirements of biologic compatibility and comfort. The sleeve, too, could be made of various suitable materials, other than those specified.

I claim:

1. A device for placement against the neck of a patient having a tracheostomy tube, said device comprising
   a tubular cushion having a through hole, and
   a flexible tie passing through the through hole, for securing the cushion against the neck adjacent the tracheostomy tube,
   wherein the tie has hook-or-loop fasteners on at least one surface thereof, for engaging a complementary surface of a tracheostomy collar worn by the patient, and the tubular cushion is slit lengthwise to admit the flexible tie laterally.

2. The device of claim 1, wherein the cushion is a sleeve made of a closed-cell polymeric foam.

3. The device of claim 2, wherein the foam sleeve has a skin on its outer surface.

4. The device of claim 2, wherein the sleeve has a length of about 2.5 inches.

5. The device of claim 2, wherein the sleeve has an outer diameter of about two inches.

6. The device of claim 1, wherein the flexible tie is made of a fabric material and has a length sufficient to enable ends of the tie to be joined in a knot behind the neck of a patient.

7. The device of claim 6, wherein the length of the tie is in the range of 30-36 inches.

8. A method of improving the comfort of a patient having a tracheostomy tube, said method comprising steps of placing a tubular cushion having a longitudinal through hole in a position against both the neck and the tracheostomy tube at the junction thereof, and securing the cushion at that position by passing a flexible tie having a hook-or- loop surface through the hole and pressing said surface at opposite ends of the tie against a complementary surface of a tracheostomy collar worn by the patient, wherein the tubular cushion is slit lengthwise to admit the flexible tie laterally.

* * * * *